United States Patent [19]

Mudiam

[11] Patent Number: 5,106,580
[45] Date of Patent: Apr. 21, 1992

[54] PROBE INSERTION AND RETRACTION TOOL

[75] Inventor: Sai S. Mudiam, Anniston, Ala.

[73] Assignee: Metal Samples Company, Inc., Munford, Ala.

[21] Appl. No.: 655,122

[22] Filed: Feb. 14, 1991

[51] Int. Cl.$^5$ ............................................. G01N 17/00
[52] U.S. Cl. ......................................... 422/53; 436/6; 73/866.5
[58] Field of Search ............................ 422/53; 436/6; 73/866.5

[56] References Cited

U.S. PATENT DOCUMENTS 4,282,181 8/1981 Pierce ..................................... 422/53
4,915,910 4/1990 Manning et al. ....................... 422/53

OTHER PUBLICATIONS

Special Retractor Tool, Accurate Corrosion Monitoring Co., *The Accurate Retractable Corrosion Coupon Holder* Mar. 1989, p. 17.
Standard Retractor Tool, Accurate Corrosion Monitoring Co., *The Accurate Retractable Corrosion Coupon Holder* Mar. 1989, p. 18.
Cosasco ® Retractable System Retractor, Rohrback Cosasco Systems, Ltd.
Probe Retractor, Rohrback Instruments, a division of Rohrback Corporation, Corrosometer ® Accessories.

*Primary Examiner*—Jill A. Johnston
*Assistant Examiner*—Lyle A. Alexander
*Attorney, Agent, or Firm*—Jennings, Carter, Thompson & Veal

[57] ABSTRACT

A probe retraction tool including a threaded split shaft connected to a packing gland in coaxial relation to a probe inserted therein. The shaft has a longitudinally coextensive slot and axial bore within which the longitudinal axis of the shaft extends in parallel relation thereto. A spinner nut is threadably connected to the shaft and has a slip ring concentrically mounted thereon for relative rotational movement. A member for securing the probe to the spinner nut is connected to the slip ring and extends within the channel to detachably connect with an upper end of the probe. A handle is connected to the spinner nut for rotating the same, thereby urging the spinner nut, the slip ring and the probe in coaxial vertical movement along the longitudinal axis of the split shaft.

10 Claims, 4 Drawing Sheets

PROBE INSERTION AND RETRACTION TOOL

FIELD OF THE INVENTION

The present invention relates to apparatus for inserting mechanical or electrical probes within an enclosed pressurized environment and subsequently retracting the probe therefrom. More particularly the present invention relates to apparatus for inserting an elongated rod into a packing gland that is connected to and communicates with the pressurized environment.

BACKGROUND OF THE INVENTION

It is common practice to test the corrosive effects of certain materials on the storage or transport apparatus in which such materials are confined by inserting a sample coupon or electrical element made from the same material as the storing or transporting apparatus within these apparatus and the material contained therein for a predetermined time. A coupon must also be removed for further analysis whereas an electrical element is replaced after its predetermined life. In unpressurized environments, such as an open tank, and low pressure environments, the coupons and electrical elements may be inserted within the container without the use of any special tools. However, when testing materials in a pressurized environment, such as a pipeline, pressure vessel, condenser and heat exchanger, the sample coupon or electrical element must be inserted and retracted from the environment without permitting communication of the pressurized environment with the atmosphere.

Packing glands currently exist through which an elongated probe is inserted in hermetically sealed engagement therein. The packing glands are detachably connected to a valve which is connected to and communicates with the pressurized environment. To insert a sample coupon or electrical element into the pressurized environment, the gland is detached from the valve and the coupon or electrical element is attached to the end of the rod extending within the gland. The gland has a chamber in which the coupon or electrical element is contained during attachment of the gland to the valve. Once the electrical element or coupon is connected to the rod and the gland is attached to the valve, the valve is opened thereby pressurizing the chamber. The rod is inserted axially within the gland thereby positioning the coupon or electrical element within the pressurized environment.

To remove the coupon or electrical element, the coupon or electrical element is retracted within the chamber by retracting the probe through the gland. The valve is closed, pressure is bled from the chamber and the gland is detached from the valve to access the coupon or the element. The probe can be manually inserted into low pressure environments, however, at higher pressures the probe cannot be inserted or safely retracted without mechanical aid.

Probe retraction tools exist for inserting probes into high pressure environments. Examples of such retractor tools are the "Standard Retractor Tool" and the "Special Retractor Tool" manufactured by Accurate Corrosion Monitoring Company. The "Special Retractor Tool" has a base, a vertically extending vertical worm gear, a plate connected to the worm gear and vertically moved thereon by the rotation of the worm gear and a means for rotating the worm gear. The base is detachably connected to a packing gland and the probe is secured to the plate in parallel relation to the worm gear. To insert the rod, the worm gear is rotated, thereby urging the shaft into the packing gland. Note that since the worm gear and the probe are not coaxial in relation, a torqueing force is exerted on the worm gear through the plate by the pressurized environment's influence on the probe. At extremely high pressures such torqueing forces could damage the retractor tool, specifically the worm gear, and at best bind the plate with the worm gear thereby hindering the vertical movement of the plate.

The "Standard Retractor Tool" has a cylindrical casing that threadably engages certain packing glands adapted for such threaded connection, an elongated screw threadably connected to the top of the casing and extending therein, a handle connected to the top of the screw for rotating the same and a means for connecting the screw to the upper end of the probe.

The use of a solid worm gear or screw to insert the probe presents a functional dilemma in that either the screw is too thin to accommodate use with extremely high pressures or, if manufactured thick enough for such pressures, the weight of the worm gear or screw makes the retraction tool cumbersome and difficult to efficiently operate.

A retractor using an oversized threaded screw shaft is best exemplified in the COSASCO Retractor which includes a base for engaging an insertion gland, the oversized screw connected to the base and extending vertically therefrom, means for engaging the probe and means for urging the probe parallel the length of the oversized screw.

A probe retractor manufactured by Rohrback Instruments, a division of Rohrback Corporation, has a pair of parallel rotatable shafts mounted in an aluminum frame with means for engaging a probe threadably mounted to both shafts. To urge the means for engaging along a vertical path, both shafts must be rotated simultaneously. The apparatus is designed for use by two operators.

SUMMARY OF THE INVENTION

The principal object of the present invention is to provide a probe retraction tool for inserting a probe into a highly pressurized environment and subsequently retracting the probe therefrom.

In support of the principal object, another object of the present invention is to provide a probe retraction tool that minimizes the torqueing forces exerted thereon and on the probe.

And still another object of the present invention is to provide a probe retraction tool that fulfills the aforementioned objects while increasing the strength to weight ratio relative to existing probe retraction tools.

These and other objects and advantages of my invention are accomplished through the use of a split shaft having a threaded outer surface and an axial bore with a longitudinal slot interrupting the thread, wherein the split shaft is detachably mounted to a packing gland in coaxial relation to an aperture extending therethrough. A spinner nut is threadably engaged on the threaded outer surface of the shaft and has a slip ring concentrically mounted thereon for rotary motion relative thereto. Means for securing a probe to the slip ring in coaxial relation to the split shaft include a key housing connected to the slip ring and extending within the channel. A handle is connected to the spinner nut for rotating the same and consequently moving the spinner nut, the slip ring, the key housing and the probe along the longitudinal axis of the split shaft. A base is connected to the lower end of the split shaft for securing the split shaft to the packing gland in coaxial relation to the probe inserted therein.

BRIEF DESCRIPTION OF THE DRAWINGS

Apparatus embodying features of my invention are depicted in the accompanying drawings which form a portion of this disclosure and wherein.

DESCRIPTION OF A PREFERRED EMBODIMENT

Figure 2:
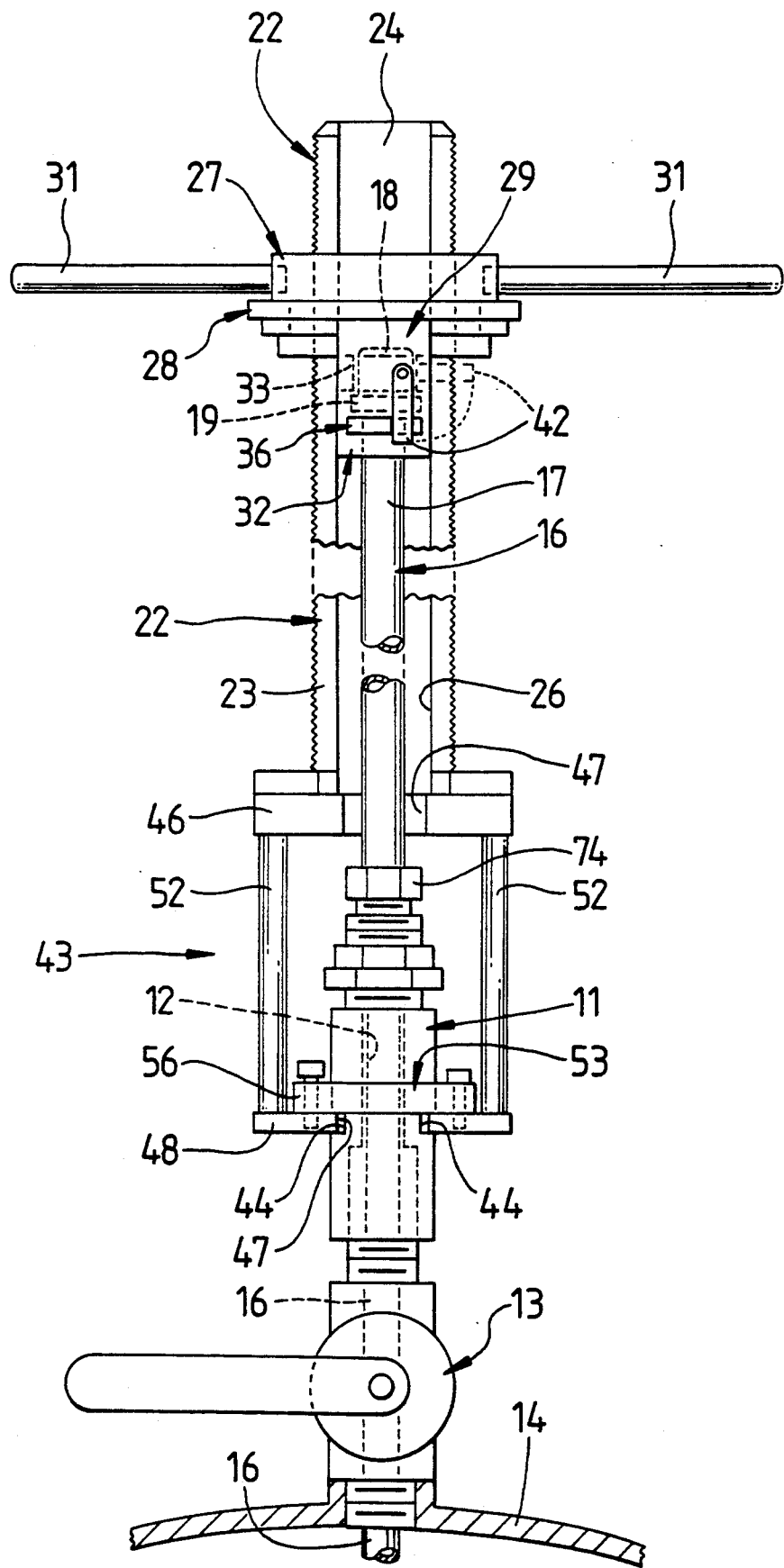
FIG. 2 is an elevational view of a first embodiment of the probe retraction tool shown engaging a typical packing gland and probe.
Figure 3:
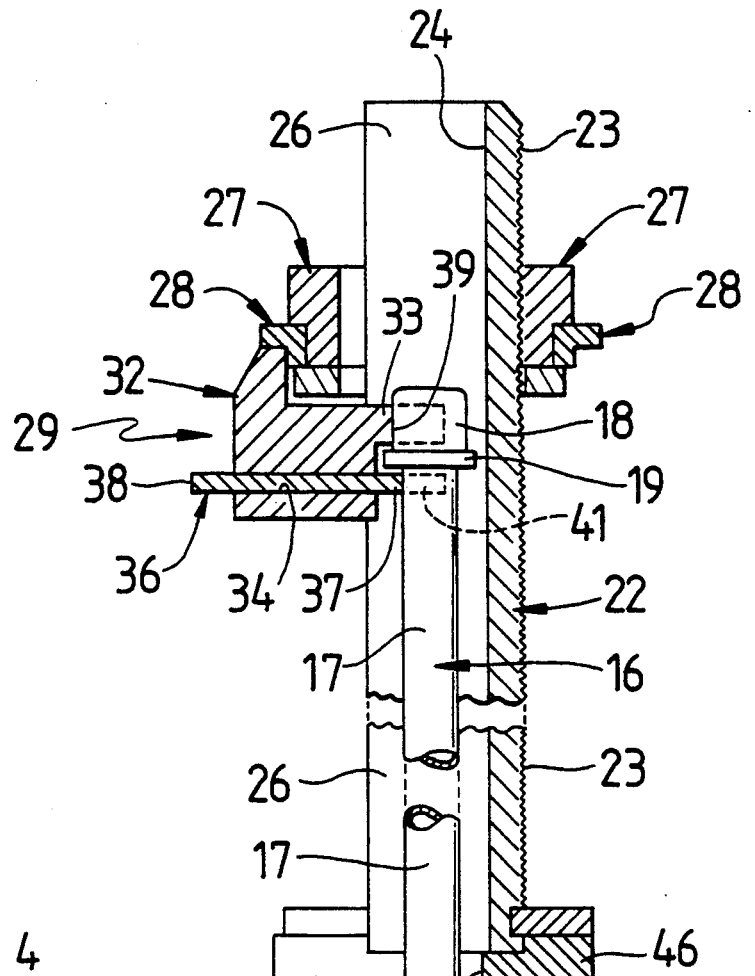
FIG. 3 is a sectional view taken along line 3—3 of FIG. 2 showing a first embodiment of the present invention.

Referring to the drawings for a clearer understanding of the invention, it should be noted that the present invention is used with a packing gland 11 shown in FIGS. 2 and 3 having an aperture 12 extending in coaxial relation therethrough. The packing gland 11 is typically connected to a valve 13 which selectively connects the interior of the packing gland 11 in communication with a pressurized environment 14. A probe 16 extends through the packing gland 11 in sealed engagement with the aperture 12. The probe 16 includes an elongated rod 17 having a head portion 18 and a shoulder 19. As shown in FIG. 3, a coupon or electrical element 21 is connected to a lower end of the rod 17 beneath the gland 11.

Figure 1:
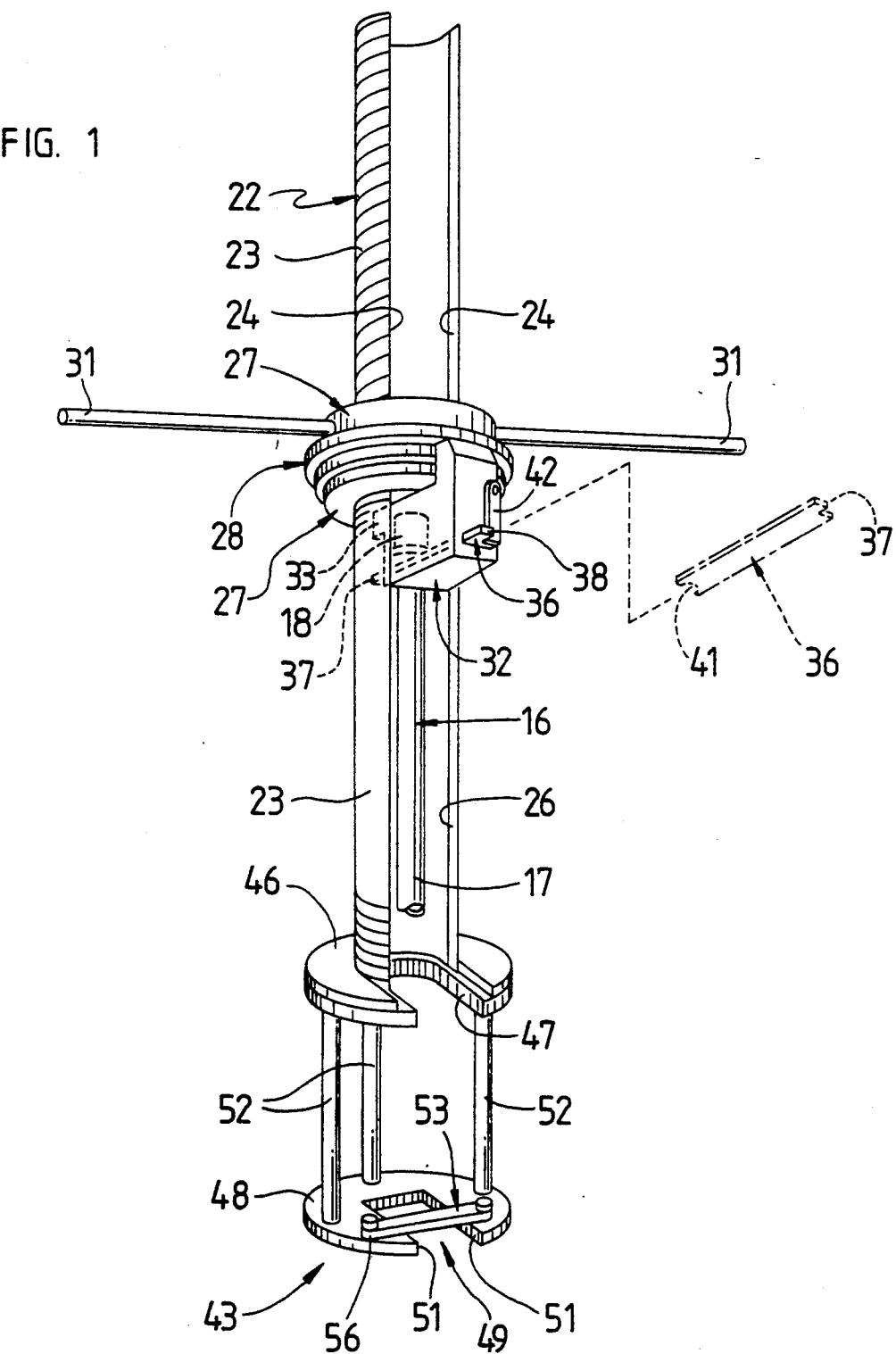
FIG. 1 is a perspective view of a first embodiment of the probe retraction tool.

As shown in FIGS. 1-3, a first embodiment of the present invention contemplates the use of an elongated split shaft 22 detachably connected to the packing gland 11 in coaxial relation to the aperture 12 and the probe 16 extending therethrough. The split shaft 22 serves as a guide having a threaded outer surface 23 and an axial bore 24. The threaded outer surface is interrupted by a longitudinal slot 26.

Mounted to the split shaft 22 for moving the probe 16 longitudinally within the split shaft 22 is a cylindrical spinner nut 27 threadably mounted to the outer surface 23 of the split shaft 22, a slip ring 28 concentrically carried by the spinner nut 27 for relative rotary movement thereon, and a securing member 29 mounted to the slip ring 28 and extending within the slot 26 and bore 24 for detachably securing the probe 16 to the slip ring 28. At least one handle 31 is connected to the spinner nut 27 for rotating the nut 27 on the threaded split shaft 22, thus moving the slip ring 28 and securing member 29 along the split shaft 22.

Figure 4:
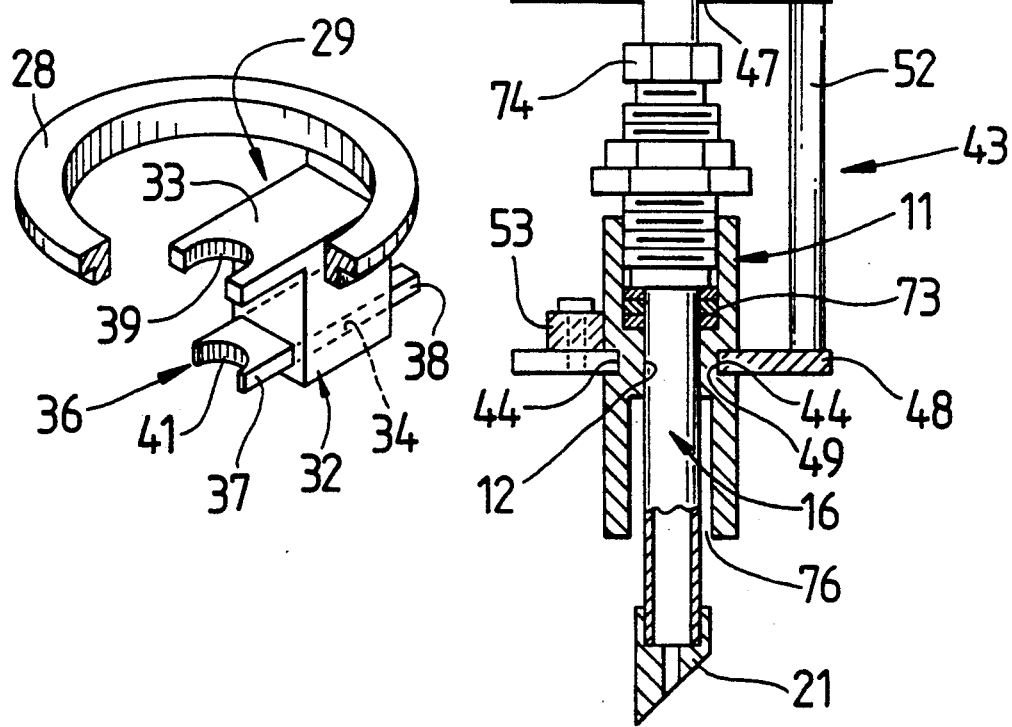
FIG. 4 is a perspective view, partially broken away showing the slip ring and securing member of the first embodiment.

As shown in FIGS. 3 and 4, the securing member 29 includes a key housing 32 connected to the slip ring 28 and extending within the bore 24. The key housing 32 has a shelf member 33 extending within the bore 24 in normal relation thereto and a rectangular slideway 34 extending below the shelf member 33 in parallel relation thereto.

An elongated key 36 is removably engaged within the slideway 34. The key 36 includes a securing end 37 that extends within the bore 24 and a lock member 38 that protrudes from the slideway 34 opposite the securing end 37. The shelf member 33 and the securing end 37 have arcuate notches 39 and 41, respectively, for receiving the probe therein. The interior of notch 39 receives the head portion 18 of the probe 16 in near contacting engagement thereof. The shoulder 19, having an outer radius greater than notch 39, is prevented from passing above the shelf member 33. The interior of notch 41 receives the rod in near contacting engagement thereof and as the shoulder 19 is also larger than notch 41, the shoulder cannot pass below the securing end 37.

As may be seen in FIGS. 1 and 2, a tab 42 is connected to the key housing 32 proximal the slideway 34 for selective rotation about a horizontal axis. When the key 36 is received within the slideway 34 the tab 42 is rotated proximal the lock member 38, thereby partially blocking the slideway 34 and preventing the retraction of the key 36 therefrom.

FIGS. 1-3 show a base 43 connected to a lower end of the split shaft 22 and slidably mounted within a pair of parallel grooves 44 formed on the packing gland 11. The base 43, thusly mounted to the packing gland 11, secures the split shaft 22 in coaxial relation to the aperture 12 and the probe 16 extending therethrough. The base 43 includes an upper plate 46 connected to the lower end of the split shaft 22 in normal relation to the longitudinal axis thereof, wherein the upper plate 46 has a notch 47 through which the probe 16 extends. The base 43 further includes a lower plate 48 mounted below the upper plate 46 in spaced relation thereto having a notch 49 with sides 51 spaced for sliding reception within the grooves 44. A plurality of rods 52 are connected intermediate said upper and lower plates 46 and 48 in normal relation thereto.

A clasp 53 is pivotally connected to the lower plate 48 for movement about a vertical axis. The clasp 53 has a secured end 54 pivotally connected to the lower plate 48 proximal notch 49 and a free end 56 that can be selectively connected to the lower plate 48 proximal notch 49, such that the clasp 53 extends across notch 49, thereby securing the base 34 to the packing gland 11.

Figure 5:
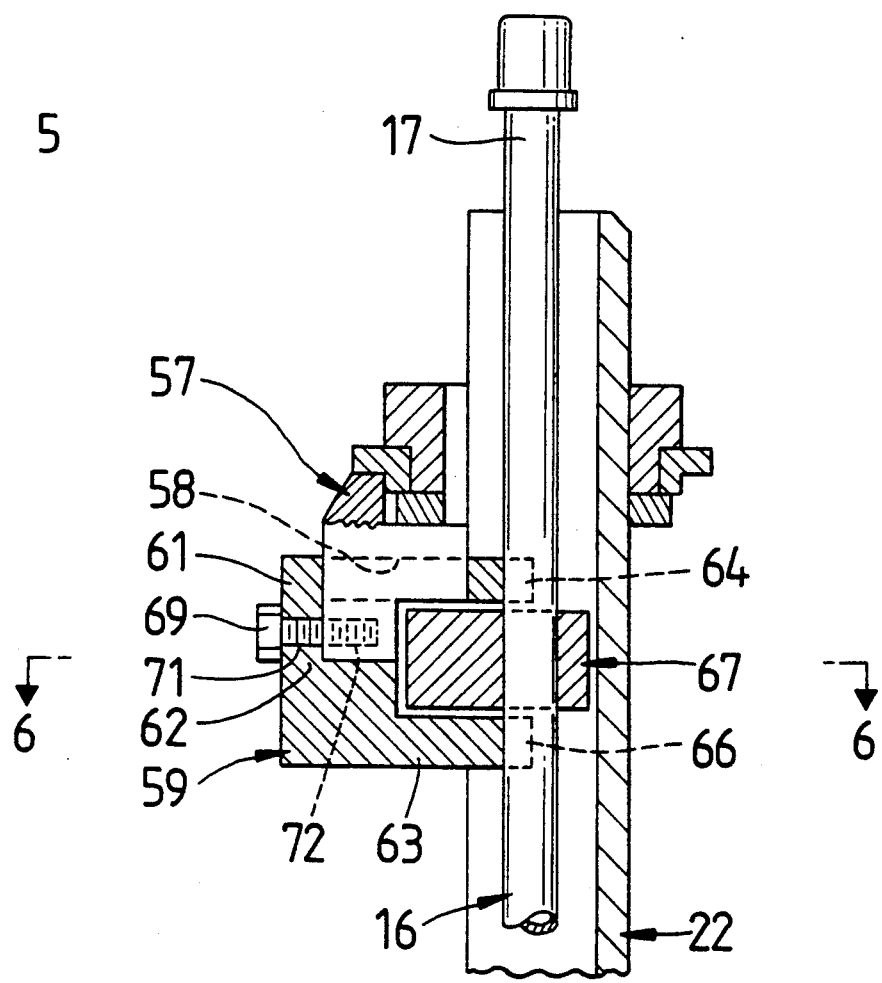
FIG. 5 is a sectional view similar to FIG. 3 showing a second embodiment of the invention.

As shown in FIG. 5, a second embodiment of the present invention contemplates the use of an insert block 57 connected to the slip ring 28 and having a slideway 58 extending therethrough in perpendicular relation to the longitudinal axis of the split shaft 22. A slide 59 is mounted to the insert block 57 and has an upper portion 61 slidably engaged within the slide receptacle 58, a back portion 62 connected to the upper portion 61 and depending therefrom adjacent the insert block 57, and a lower portion 63 connected to the back portion 52 and extending below the insert block 57 in spaced parallel relation to the upper portion 61.

Figure 6:
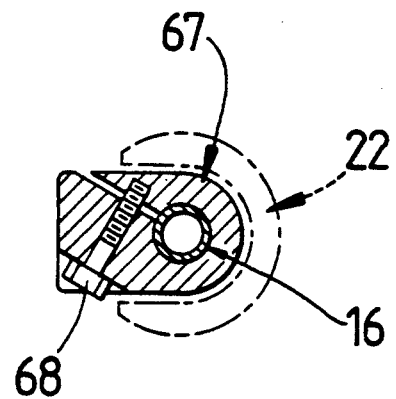
FIG. 6 is a sectional view taken along line 6—6 of FIG. 5.

The upper and lower portions 61 and 63 each extend within the bore 24 and define upper and lower slots 64 and 66, respectively, in which the probe 16 is received. A split collet 67 is detachably connected to the probe 16 intermediate the upper and lower portions 61 and 63. As shown in FIG. 6, the split collet 67 is tightened about the probe 16 by a set screw 68 threadably received within the collet 67. The upper and lower portions 61 and 63, detachably secure the collet 67 and thus the probe 16 to the insert block 57 and the slip ring 28 for vertical movement therewith, whereby moving the block 57 causes either the upper portion 61 or lower portion 63 to contact the collet 67, thus facilitating longitudinal movement of the probe 16 along the split shaft 22.

A threaded bolt 69 extends through a first bore 71 formed in the back portion 62 and is threadably received in a second bore 72 formed in the insert block 57. The bolt 69, thus received, retains the upper portion 61 within the slide receptacle 58.

In operation, the first embodiment of the invention is used with probes 16 having a fixed length no greater than the distance from the valve to the top of the split shaft, wherein the head portion 18 of the probe 16 does not extend above the split shaft 22 when the probe is in a fully retracted position. To insert the probe 16 into the pressurized environment, the rod 17 of probe 16 is inserted into the aperture 12 of packing gland 11 with the gland 11 being temporarily detached from the valve 13. The gland 11 includes sealing elements 73 which receive the rod 17 in hermetically sealed contact therewith. Locking member 74 is provided to selectively secure the probe in a non-sliding position; however, during the insertion and retraction of probes having a fixed insertion depth, the locking member 74 remains in an unlocked position. Once the rod 17 is inserted through the aperture 12, the coupon or electrical element 21 is attached to a lowermost end of the rod 17 and is withdrawn within a chamber 76 defined by a lower end of gland 11. The gland 11 is threadably connected to the valve 13 which is in a closed position. The base 43 is fitted around the gland 11 with the sides 51 of lower plate 48 being received within the grooves 44. The clasp 53 is secured across the notch 49 thereby securing the base 43 to the packing gland 11. The probe 16 is coaxially received within the bore 24 as the base 43 is connected to the gland 11. The handle 31 and spinner nut 27 are rotated to urge the key housing 32 downward and adjacent the probe 16, wherein the head portion 18 is received in notch 39 and the shelf member 33 is urged in contact with the shoulder 19. The key 36 is inserted within the rectangular slideway 34 to engage the rod 17 below the shoulder 19. Rotating the handle 31 and spinner nut 27 to urge the key housing 32 in a downward direction will urge the probe 16 longitudinally within the pressurized environment 14. When the probe 16 is inserted a selected distance within the pressurized environment 14, the locking member may be manually actuated to a locked position, thereby preventing the longitudinal movement of the probe 16. Apparatus for grasping and locking a rod within an aperture are common in the industry and since such apparatus are not critical to the present invention, further detail as to their construction has been omitted. The probe 16 can be retracted from the pressurized environment by reversing the rotation of the handle 31 and spinner nut 27. The retraction of the coupon or clement through the valve 13 and into chamber 76 permits the valve 13 to be closed so the probe 16 may be disengaged from the gland 11.

The second embodiment of the invention is used to insert a probe 16 having a length substantially longer than the split shaft 22. Such a probe 16 is manually inserted within the gland 11 and the base is connected to gland 11 as previously described. Before the valve 13 is opened, the locking member 74 is manually actuated to a locked position. A collet 67 is connected to the probe 16, as shown in FIGS. 5 and 6, at a selected height thereon and within the axial bore 24. The insert block 57 is urged adjacent the collet 67 by rotating the handle 31 and spinner nut 27 as previously described. The upper portion 61 of the slide 59 is inserted through slideway 58 and engages the rod 17 above collet 67. Accordingly, the lower portion 63 engages the rod 17 below the collet 67. The back portion 62 is secured in abutment with the insert block 57 by the threaded reception of the bolt 69 within the second bore 72. Once the slide 59 is positioned about the collet 67, the locking member 74 is manually placed in an unlocked position. The probe 16 is inserted within the gland 11 a selected distance using the handle and spinner nut as previously described, whereafter the locking member is again placed in a locked position. The collet 67 is attached to the rod 17 at a selected height above its previous connection and the process is repeated until the probe 16 has been inserted a preselected distance within the pressurized environment 14. From the foregoing, it should be clear that the present invention provides an apparatus that safely and efficiently controls the insertion and retraction of a probe from a pressurized environment while minimizing the torqueing forces exerted on the probe and while providing an increased strength to weight ratio relative to existing probe retraction tools.

While I have shown my invention in various forms, it will be obvious to those skilled in the art that it is not so limited but is susceptible of various changes and modifications without departing from the spirit thereof.

What I claim is:

1. Apparatus for inserting a corrosion monitoring probe into and retracting said probe from an enclosed pressurized environment having a packing gland through which said probe is inserted, comprising:
   (a) a means for monitoring corrosion within said environment;
   (b) an elongated split shaft detachably connected to said packing gland in coaxial relation to said probe, wherein said split shaft has an interrupted threaded outer surface and an axial bore; and
   (c) means threadably mounted to said split shaft adapted to maintain and move said monitoring means along the axial bore of said split shaft into the pressurized environment.

2. Apparatus as described in claim 1 wherein said moving means comprises:
   (a) a cylindrical spinner nut threadably mounted to said split shaft;
   (b) a slip ring concentric with and carried by said spinner nut for relative rotary movement therewith; and
   (c) means mounted to said slip ring and extending within said axial bore for detachably securing said monitoring means to said slip ring.

3. Apparatus as described in claim 2 wherein said securing means comprises:
   (a) a key housing connected to said slip ring and having a shelf member extending within said axial bore and a slideway extending therethrough in parallel relation to said shelf member; and
   (b) an elongated key removably engaged within said slideway and having a securing end that extends within said axial bore and a lock member that protrudes from said slideway opposite said securing end, wherein said shelf member and said securing end are notched to receive said monitoring means therein, said monitoring means having a shoulder located intermediate said shelf member and said securing end, against which either said shelf member or said elongated end will contact pursuant to the movement of said insert block along said shaft.

4. Apparatus as described in claim 3 comprising a tab mounted to said key housing proximal said slideway for movement about a horizontal axis, wherein said tab secures said key within said slideway when said tab is rotated adjacent said lock member and across said passageway.

5. Apparatus as described in claim 2 wherein said securing means comprises:
   (a) an insert block connected to said slip ring and having a slideway extending therethrough in perpendicular relation to the longitudinal axis of said split shaft;
   (b) a slide mounted to said insert block having an upper portion slidably engaged within said slideway, a back portion connected to said upper portion and depending therefrom adjacent said insert block, and a lower portion connected to said back portion and extending below said insert block in spaced parallel relation to said upper portion, wherein said upper and lower portions each extend within said axial bore and define upper and lower slots, respectively, in which said monitoring means is received; and
   (c) a collet detachably connected to said monitoring means intermediate said upper and lower portions for securing said monitoring means relative thereto.

6. Apparatus as described in claim 5 wherein said securing means further comprises means connected to said insert block and said slide for retaining said upper portion within said slideway.

7. Apparatus as described in claim 2 comprising at least one radially extending handle connected to said spinner nut.

8. Apparatus as described in claim 2 comprising a base connected to a lower end of said split shaft and slidably mounted around said packing gland and within a pair of parallel grooves formed on said packing gland, wherein said base, when mounted to said packing gland, secures said split shaft in coaxial relation to said monitoring means.

9. Apparatus as described in claim 8 wherein said base comprises:
   (a) an upper plate connected to said lower end of said split shaft and having a first notch through which said monitoring means extends;
   (b) a lower plate mounted to said upper plate in spaced relation thereto having a second notch with sides spaced for sliding reception within said grooves; and
   (c) a plurality of rods connected intermediate said upper and lower plates in normal relation thereto.

10. Apparatus as described in claim 9 comprising a clasp pivotally connected to said lower plate for movement about a vertical axis, wherein said clasp is selectively pivoted across said second notch and detachably secured thereacross to secure said base to said packing gland.

* * * * *